United States Patent
Rome et al.

(10) Patent No.: US 9,381,036 B2
(45) Date of Patent: Jul. 5, 2016

(54) TUNNELER WITH AN EXPANDABLE ATTACHMENT MECHANISM

(75) Inventors: Guy Rome, West Valley, UT (US); William R. Barron, Riverton, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 2220 days.

(21) Appl. No.: 11/021,769

(22) Filed: Dec. 21, 2004

(65) Prior Publication Data
US 2006/0135949 A1    Jun. 22, 2006

(51) Int. Cl.
*A61B 17/34* (2006.01)
*A61B 17/32* (2006.01)
*A61M 39/12* (2006.01)

(52) U.S. Cl.
CPC . *A61B 17/3415* (2013.01); *A61B 2017/320044* (2013.01); *A61B 2017/320056* (2013.01); *A61M 39/12* (2013.01)

(58) Field of Classification Search
CPC .............. A61B 17/3415; A61B 2017/320044; A61B 2017/320056; A61M 39/12
USPC .......... 285/243; 600/184; 604/533, 523, 534, 604/535; 606/108, 190; 294/96; 81/445
See application file for complete search history.

(56) References Cited

U.S. PATENT DOCUMENTS

| | | | | |
|---|---|---|---|---|
| 1,390,564 A * | 9/1921 | Knorr | ............................ | 285/243 |
| 2,280,892 A * | 4/1942 | Cowles | ......................... | 285/243 |
| 2,497,633 A * | 2/1950 | Shapiro et al. | .................. | 81/445 |
| 2,719,747 A * | 10/1955 | Layne | ............................. | 294/89 |
| 3,724,882 A | 4/1973 | Dehar | | |
| 4,062,573 A * | 12/1977 | Fleischer | ...................... | 285/116 |
| 4,143,893 A | 3/1979 | Fleischer | | |
| 4,643,472 A * | 2/1987 | Schukei et al. | ................. | 294/94 |
| 4,672,979 A | 6/1987 | Pohndorf | | |
| 4,746,158 A * | 5/1988 | Fields | ............................. | 294/94 |
| 5,094,496 A * | 3/1992 | King, Sr. | ......................... | 294/96 |
| 5,214,868 A * | 6/1993 | Persbacker | ...................... | 37/94 |
| 5,306,240 A | 4/1994 | Berry | | |
| 5,405,329 A | 4/1995 | Durand | | |
| 5,624,413 A | 4/1997 | Markel et al. | | |

(Continued)

FOREIGN PATENT DOCUMENTS

| GB | 2012595 A | 8/1979 |
|---|---|---|
| GB | 2103936 A | 3/1983 |

(Continued)

OTHER PUBLICATIONS

U.S. Appl. No. 10/888,817, filed Jul. 8, 2004 Advisory Action dated Aug. 26, 2009.

(Continued)

*Primary Examiner* — Thomas McEvoy
(74) *Attorney, Agent, or Firm* — Rutan & Tucker, LLP

(57) ABSTRACT

A tissue tunneler including an expandable attachment mechanism for securing a catheter. In one variation, the tissue tunneler comprises an elongate tunneler with a protrusion extending from the proximal end of the tunneler. An expansion mechanism is provided on the protrusion for insertion into the catheter. An oversleeve slidably disposed over the elongated tunneler may be provided to engage the expansion mechanism and trap the catheter between the oversleeve and the expansion mechanism. In another variation, the expansion mechanism may comprise of an expandable O-ring configured to engage an inner surface within a catheter.

20 Claims, 14 Drawing Sheets

(56) References Cited

U.S. PATENT DOCUMENTS

| | | | |
|---|---|---|---|
| 5,647,627 A * | 7/1997 | Baessler | 294/96 |
| 5,718,692 A | 2/1998 | Schon et al. | |
| 5,762,631 A | 6/1998 | Klein | |
| 5,776,111 A | 7/1998 | Tesio | |
| 5,944,732 A | 8/1999 | Raulerson et al. | |
| 5,947,953 A | 9/1999 | Ash et al. | |
| 5,988,719 A * | 11/1999 | Lavender | 294/96 |
| 6,190,349 B1 | 2/2001 | Ash et al. | |
| 6,282,999 B1 * | 9/2001 | Hite et al. | 81/445 |
| 6,360,636 B1 * | 3/2002 | Elftmann | 81/445 |
| 6,428,256 B2 * | 8/2002 | Wieser | 411/60.3 |
| 6,475,244 B2 | 11/2002 | Herweck et al. | |
| 6,638,242 B2 | 10/2003 | Wilson et al. | |
| 6,682,519 B1 | 1/2004 | Schon | |
| 6,695,832 B2 | 2/2004 | Schon et al. | |
| 6,718,707 B2 * | 4/2004 | Marshall | 52/223.13 |
| 6,719,749 B1 | 4/2004 | Schweikert et al. | |
| 6,796,741 B1 * | 9/2004 | DeVaull et al. | 405/128.5 |
| 6,872,198 B1 | 3/2005 | Wilson et al. | |
| 6,881,211 B2 | 4/2005 | Schweikert et al. | |
| 6,921,396 B1 | 7/2005 | Wilson et al. | |
| 7,393,339 B2 | 7/2008 | Zawacki et al. | |
| 7,396,060 B2 * | 7/2008 | Huncovsky | 294/96 |
| 2004/0006329 A1 | 1/2004 | Scheu | |
| 2004/0039372 A1 | 2/2004 | Carmody | |
| 2004/0065333 A1 | 4/2004 | Wilson et al. | |
| 2004/0092863 A1 | 5/2004 | Raulerson et al. | |
| 2004/0122418 A1 | 6/2004 | Voorhees | |
| 2004/0146679 A1 * | 7/2004 | Suzuki et al. | 428/36.91 |
| 2004/0171997 A1 | 9/2004 | Wilson et al. | |
| 2004/0172003 A1 | 9/2004 | Wilson et al. | |
| 2004/0176739 A1 | 9/2004 | Stephens et al. | |
| 2004/0193119 A1 | 9/2004 | Canaud et al. | |
| 2004/0230204 A1 | 11/2004 | Wortley et al. | |
| 2005/0027282 A1 | 2/2005 | Schweikert et al. | |
| 2005/0085765 A1 | 4/2005 | Voorhees | |
| 2005/0096585 A1 | 5/2005 | Schon et al. | |
| 2005/0187535 A1 | 8/2005 | Wilson et al. | |
| 2005/0228364 A1 | 10/2005 | Braga | |
| 2006/0009783 A1 | 1/2006 | Rome et al. | |
| 2006/0095062 A1 | 5/2006 | Stephens | |
| 2009/0221950 A1 | 9/2009 | Atkins | |

FOREIGN PATENT DOCUMENTS

| | | |
|---|---|---|
| WO | 9801182 A1 | 1/1998 |
| WO | 9915220 A1 | 4/1999 |
| WO | 0023137 A1 | 4/2000 |
| WO | WO 2007/037876 | 4/2007 |

OTHER PUBLICATIONS

U.S. Appl. No. 10/888,817, filed Jul. 8, 2004 Final Office Action dated Jun. 18, 2009.

U.S. Appl. No. 10/888,817, filed Jul. 8, 2004 Non-Final Office Action dated Sep. 5, 2008.

* cited by examiner

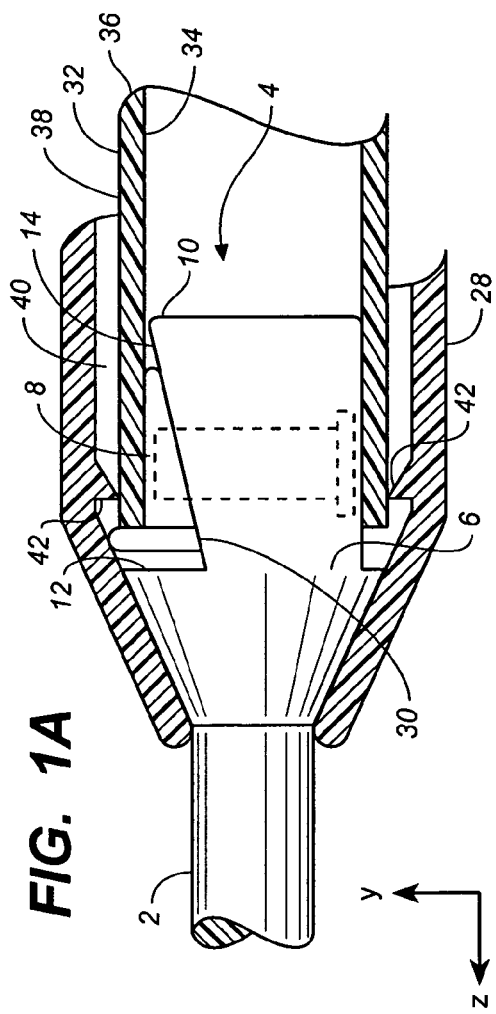
FIG. 1A
FIG. 1B
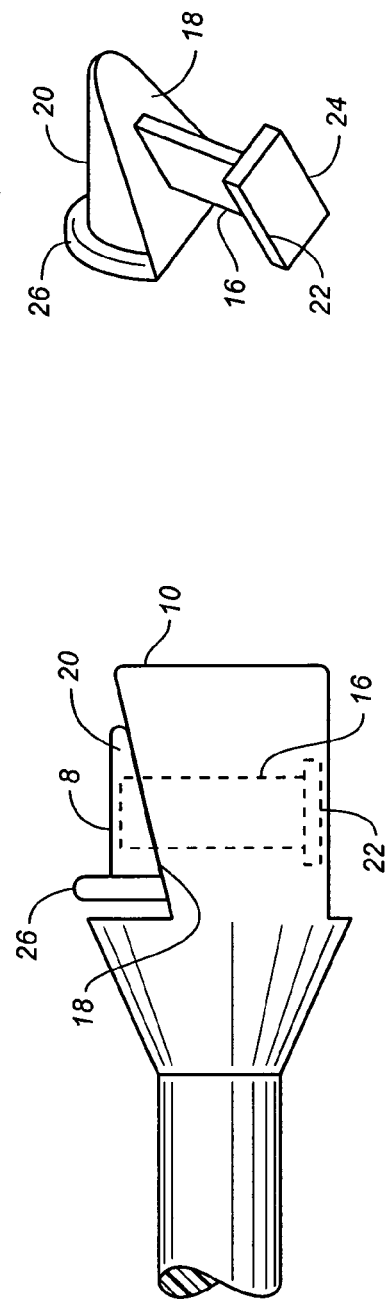
FIG. 1C

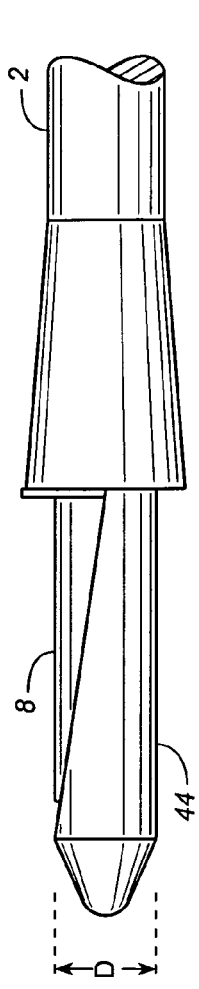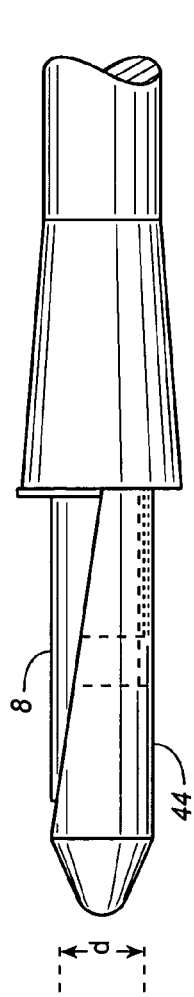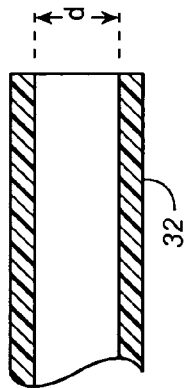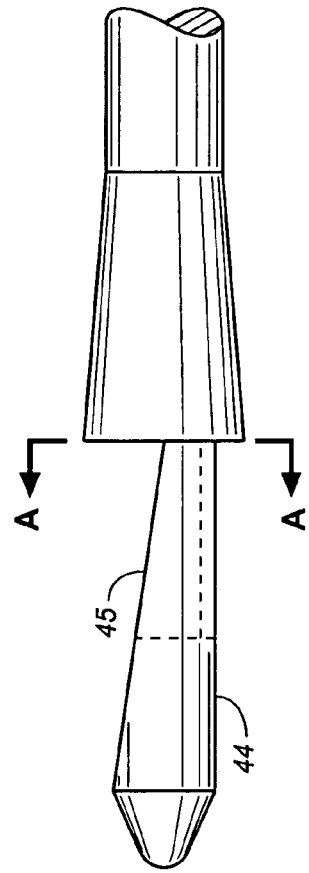
FIG. 2A
FIG. 2B
FIG. 2C
FIG. 2D (Section A-A)

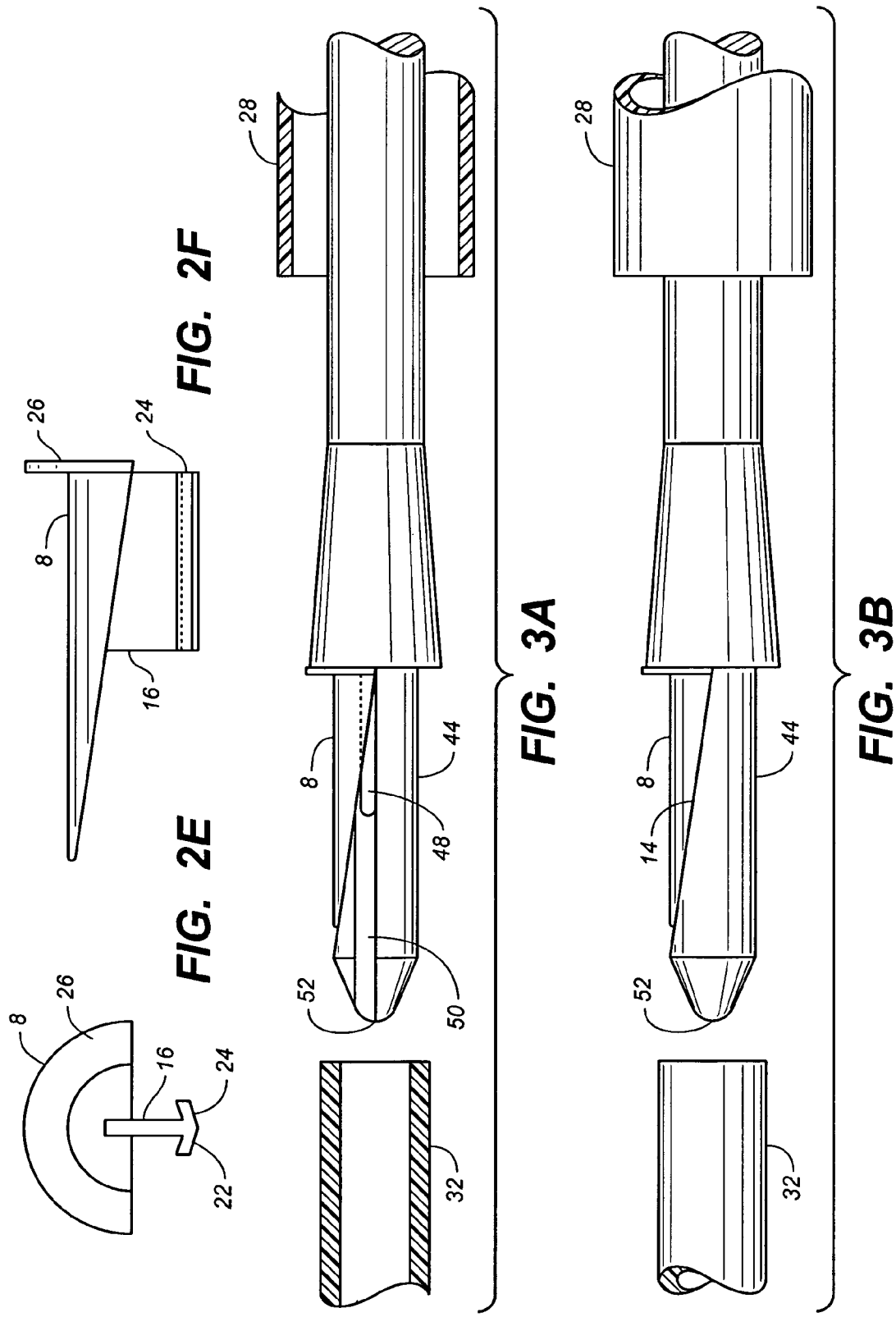

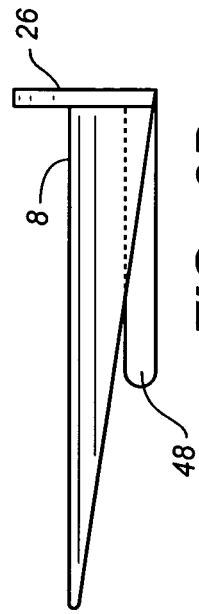
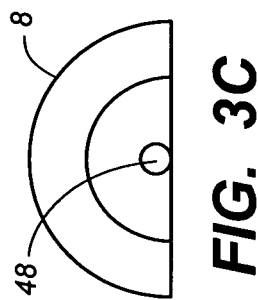
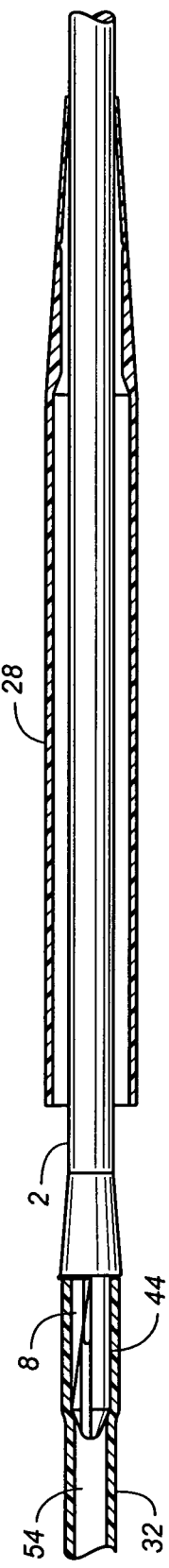

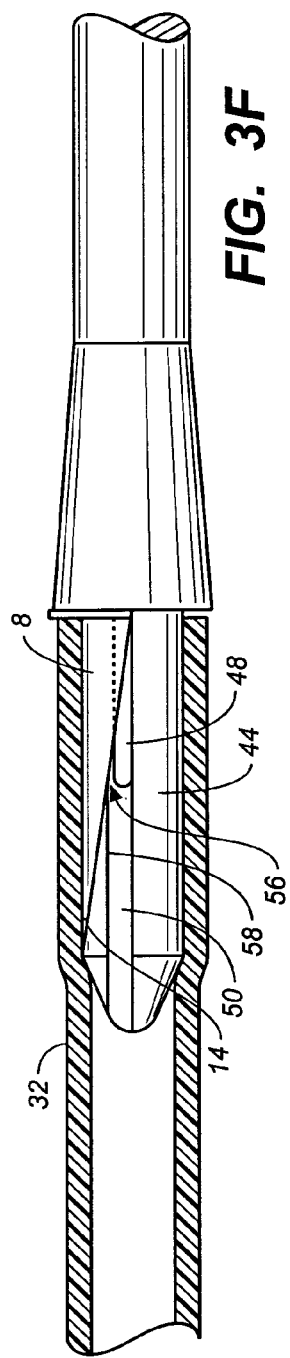
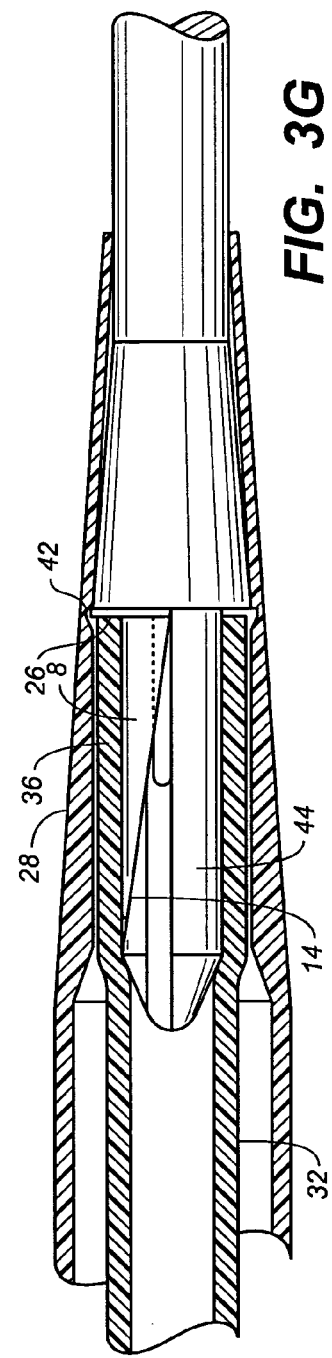
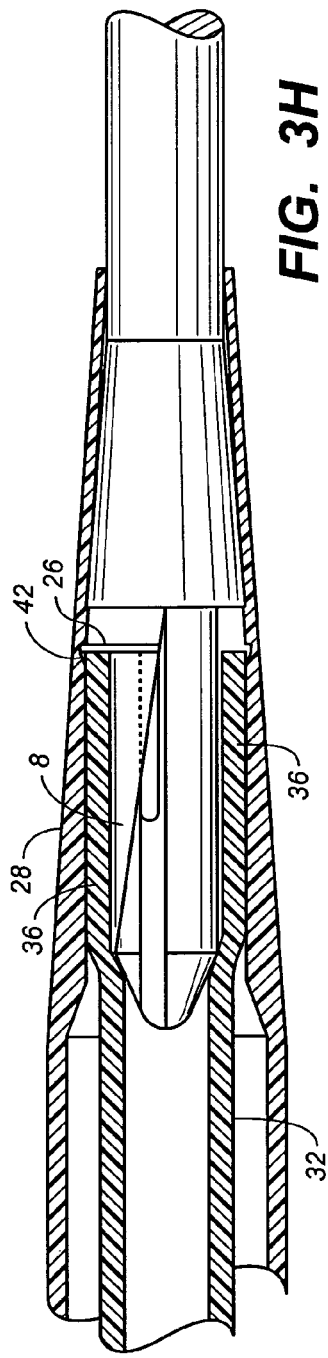

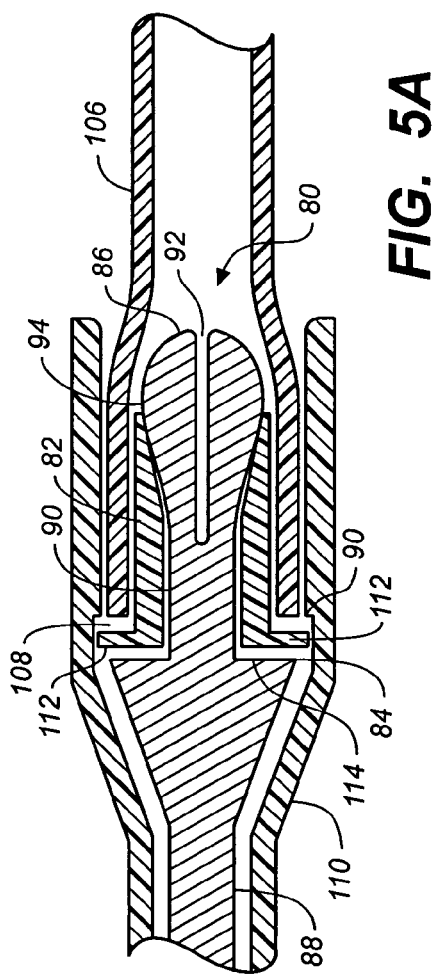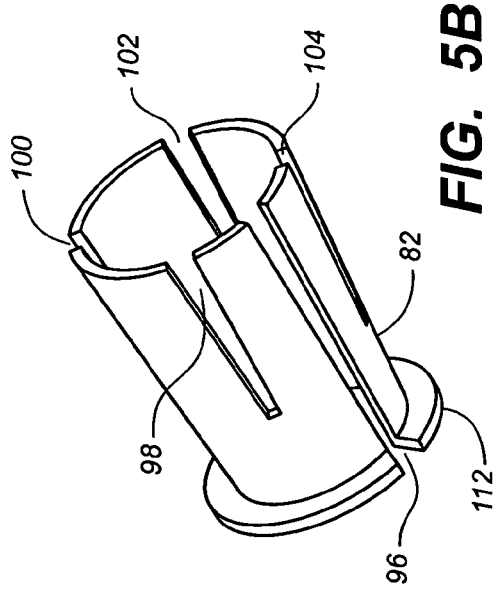

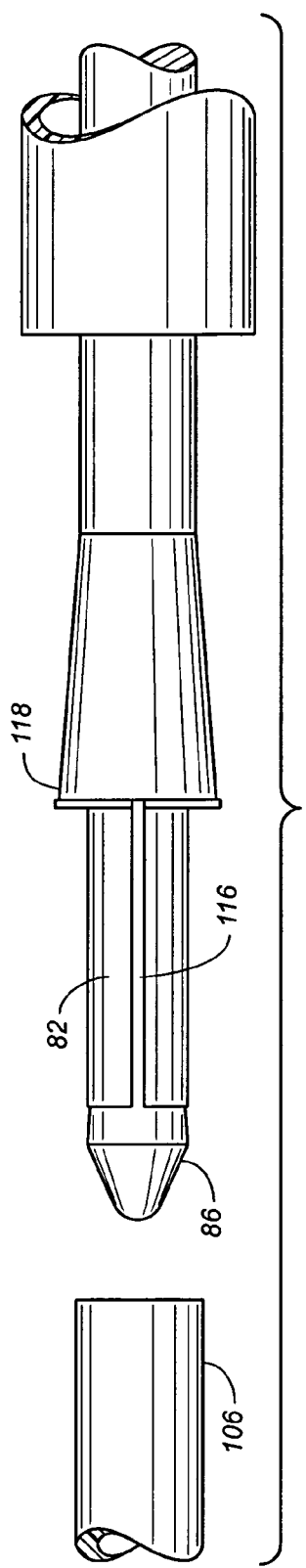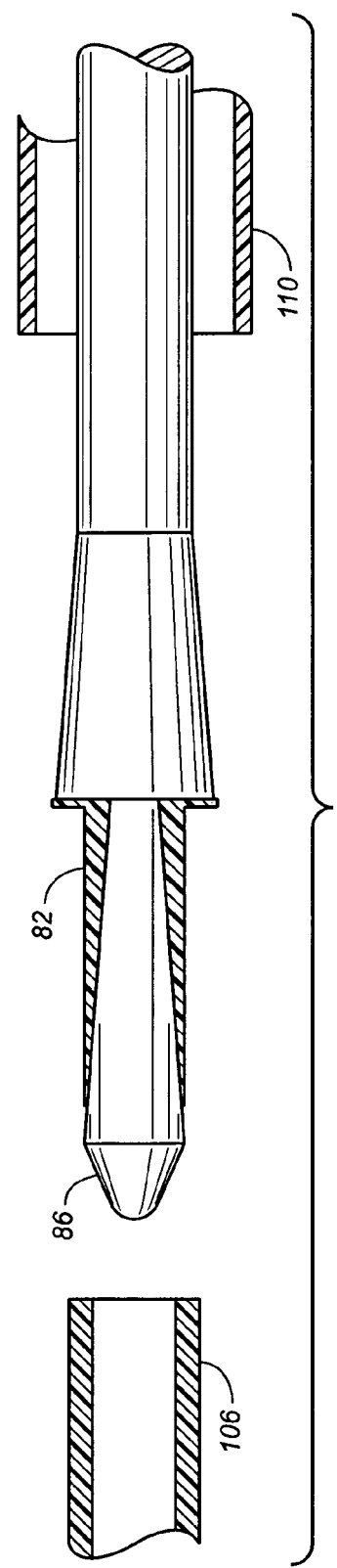
FIG. 6A
FIG. 6B
FIG. 6C
FIG. 6D

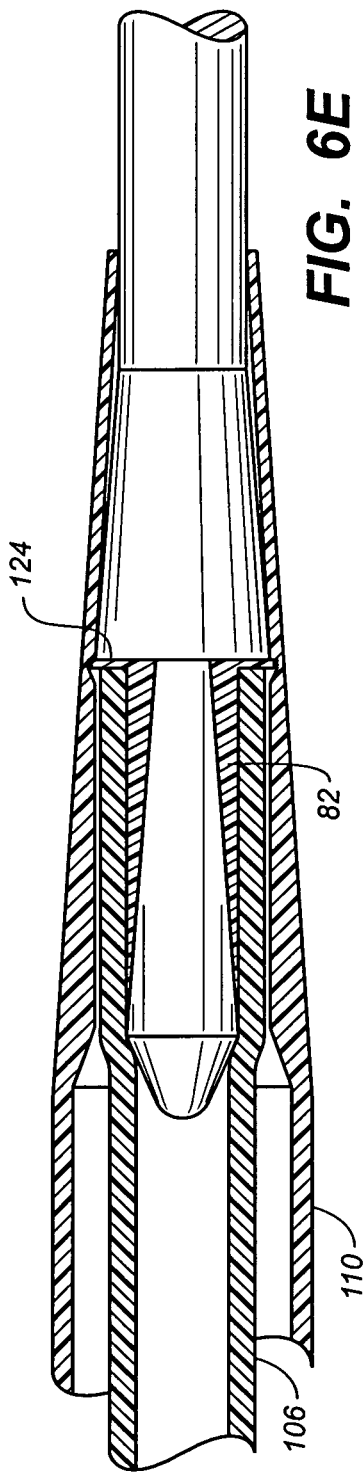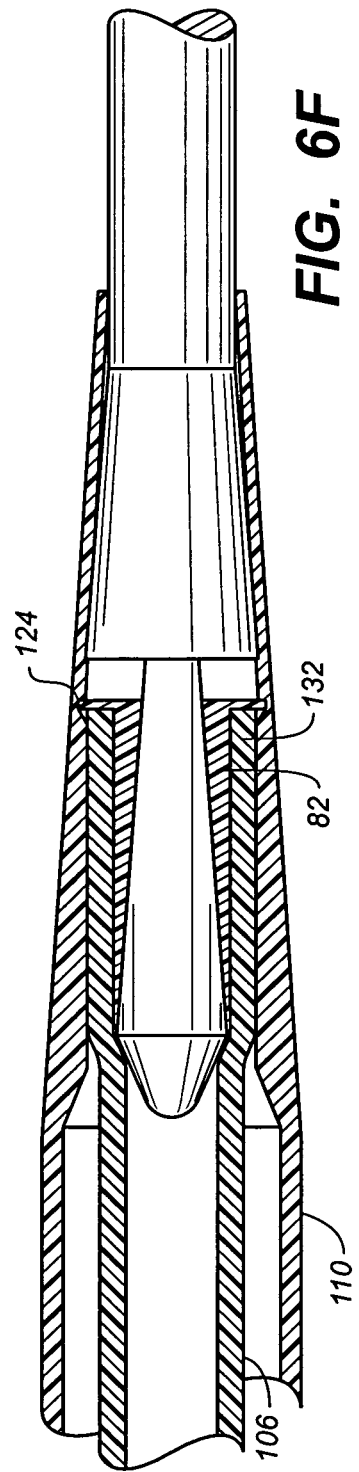

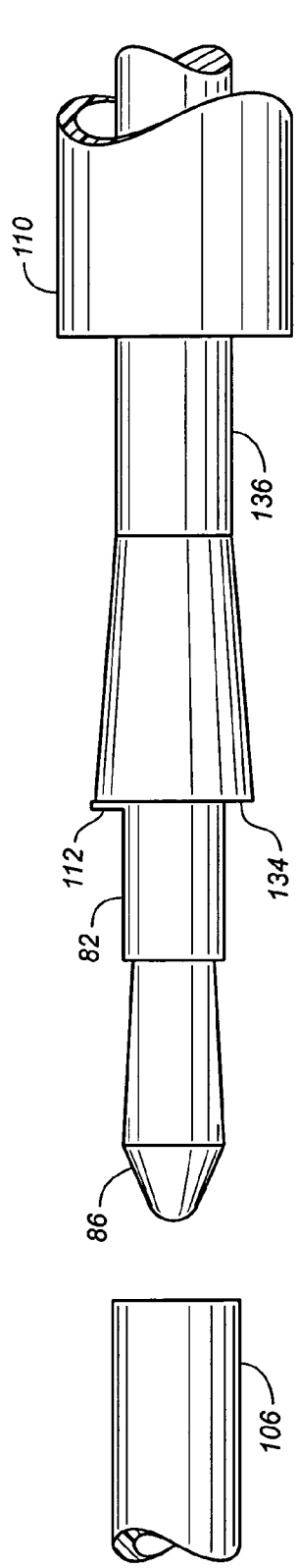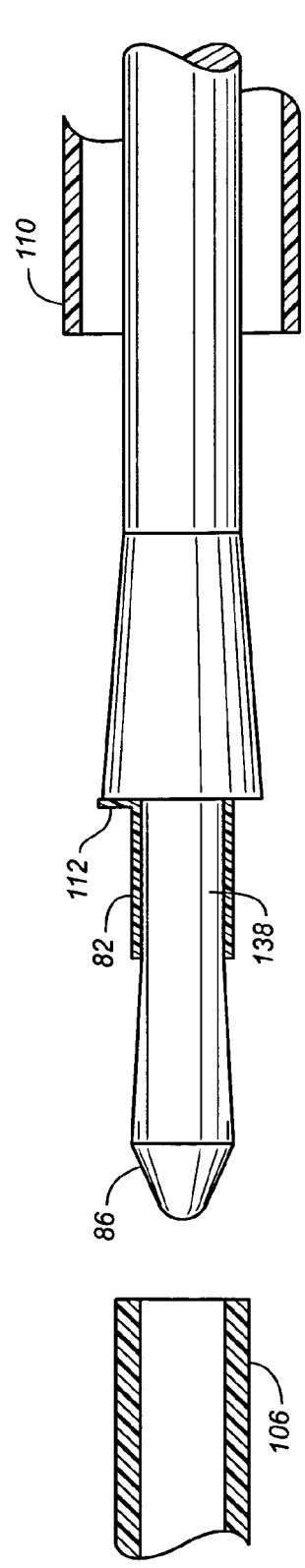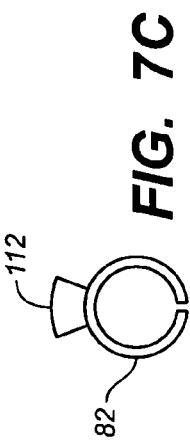

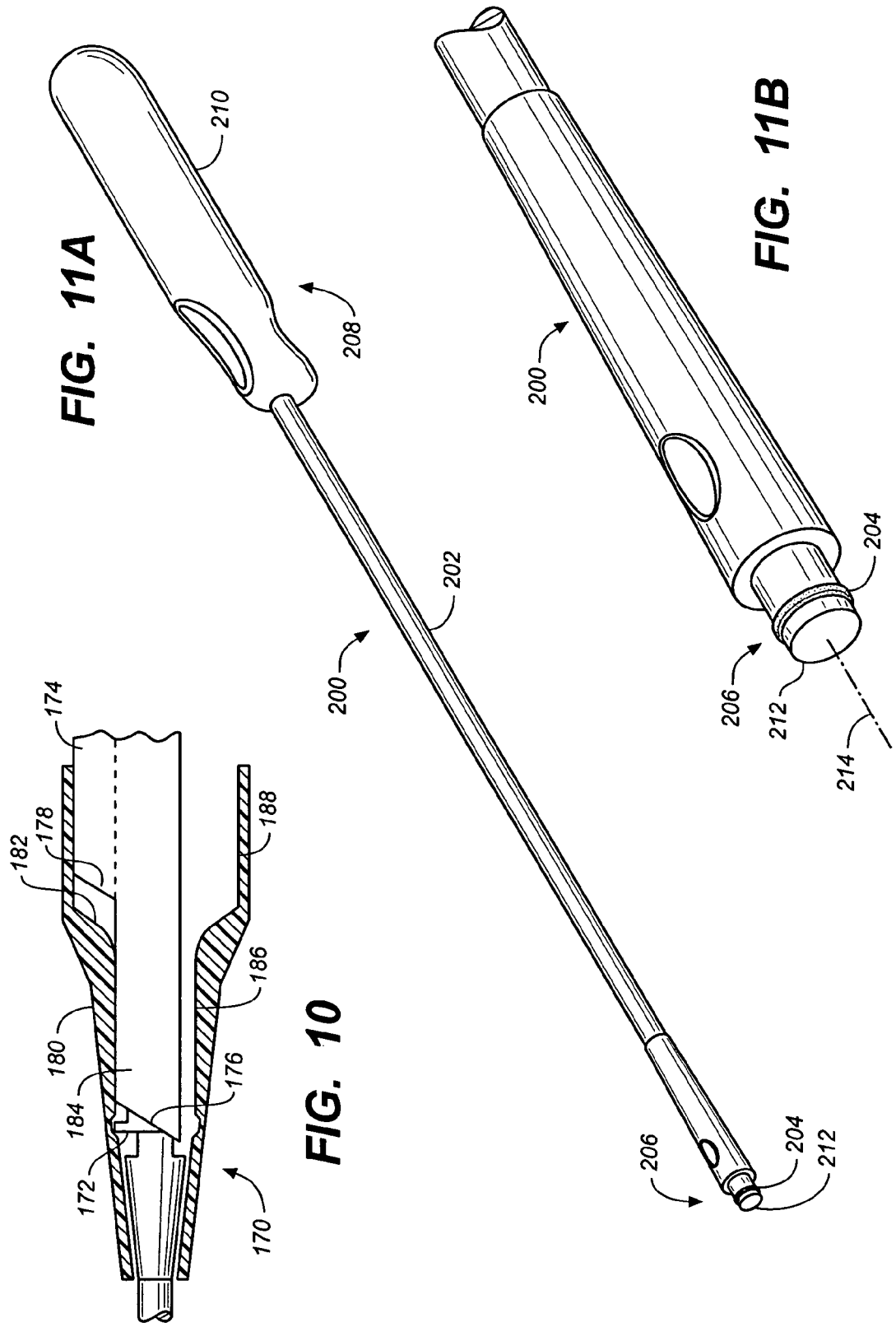

TUNNELER WITH AN EXPANDABLE ATTACHMENT MECHANISM

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

In various medical applications an implanted catheter is needed to access a patient's circulatory system. The implanted catheter may be utilized, for example, for delivery of medication/fluids or retrieval/sampling of blood. For example, it may be desirable to establish a central line (i.e., access to a large vein) for infusion of medications, chemotherapy drugs, antibiotics, anti-nausea medications, blood products, nutrients or fluids. Implanted catheters are also used in dialysis, apheresis, and other applications requiring diversion of a part of the blood flow in the circulatory system for processing or filtering. However, a common problem associated with implanted catheters is the increased risk of infection due to the establishment of this artificial path into the patient's body. The risk of infection increases the longer the catheter remains implanted.

One common approach to decrease the risk of infection is to "tunnel" the proximal end (i.e., the physician access end) of the catheter within the patient's body such that the catheter enters the body at a location that is displaced from the location where the catheter enters a major blood vessel within the patient's body. For example, a central line may be established by inserting a catheter into the subclavian vein that runs behind the clavicle, but the catheter entry point into the patient's body may be moved away from an area next to the clavicle to an area that is not immediately above the entry point into the subclavian vein. In this process, the actual access to the subclavian vein is still achieved by a puncture under the clavicle, but the proximal portion of the catheter is pulled under the skin for about 2-4 inches and emerges from the body at a location close to the nipple. This procedure may allow the catheter to stay in place for weeks to months, or even, in some circumstances, for years.

A tunneler may be utilized to assist in the tunneling of a catheter from a surface entry location on the patient's body to a location where the catheter actually enters a vessel into the circulatory system. Such a tunneler is generally made of steel or hard plastic and has a tapered distal end for tunneling through bodily tissue. Typically, the proximal end of the tunneler has a barb for insertion into the lumen of the catheter. An oversleeve is then typically forced onto the portion of the catheter that has been expanded by the barb. In one application, the catheter placement is accomplished by first making a cut-down incision near the neck of the patient, and then making an exit site incision remote from the cut-down incision. The catheter is attached to the tunneler by forcing the proximal barbed end thereof into the lumen of the catheter and sliding a sleeve over the catheter. A sleeve with a larger outer diameter may be used so that when the tunnel is made, the hole created is sufficiently large to prevent constricting forces from acting on the catheter as it resides in the tunnel. The tunneler with catheter attached is then pushed from the exit site incision toward the cut-down incision, creating a subcutaneous tunnel. When the tip of the tunneler emerges at the cut-down site, it is grasped by the physician, who pulls it through until reaching the sleeve on the tunneler. The sleeve is then pushed off the catheter and the proximal end of the tunneler is pulled out from the catheter lumen. The catheter distal end is then placed into the blood vessel.

Examples of various tunneling and gripping devices are disclosed in U.S. Patent Application Pub. No. US 2004/0006329 A1, titled "DEVICE FOR HOLDING AND GUIDING A GUIDE-WIRE IN A CATHETER" by Scheu, published Jan. 8, 2004; U.S. Patent Application Pub. No. US 2004/0039372 A1, titled "OVER-THE-WIRE CATHETER HAVING A SLIDABLE INSTRUCMENT FOR GRIPPING A GUIDE-WIRE" by Carmody, published Feb. 26, 2004; U.S. Pat. No. 3,724,882, titled "TUBE-TO-HOSE CONNECTION" issued to Dehar, dated Apr. 3, 1973; U.S. Pat. No. 4,143,893, titled "CLAMPING DEVICE" issued to Fleischer, dated Mar. 13, 1979; U.S. Pat. No. 4,672,979, titled "SUTURE SLEEVE ASSEMBLY" issued to Pohndorf, dated Jun. 16, 1987; U.S. Pat. No. 5,306,240, titled "TUNNELER AND METHOD FOR IMPLANTING SUBCUTANEOUS VASCULAR ACCESS GRAFTS" issued to Berry, dated Apr. 26, 1994; U.S. Pat. No. 5,405,329, titled "INTRAVASCULAR MULTI-LUMEN CATHETER, CAPABLE OF BEING IMPLANTED BY "TUNNELING" issued to Durand, dated Apr. 11, 1995; and U.S. Pat. No. 6,475,244 B2, titled "TUNNELING DEVICE" issued to Herweck et al., dated Nov. 5, 2002; each of which is incorporated herein by reference in its entirety.

One of the disadvantages of the current tunneling devices is that attachment and removal of the barbed end of the tunneler from the lumen of the catheter often results in damage to the lumen and the distal tip of the catheter. Typically, the barb is much larger than the diameter of the catheter lumen and thus forces the tip of the catheter to expand radially and makes the tip prone to damage. Moreover, with respect to the typical use of an oversleeve, the axial motion along the length of the tunneler, which pushes the oversleeve onto the expanded catheter over the barb or pulls the oversleeve off the expanded catheter over the barb, may cause significant abrasion on the exterior of the catheter body. In addition, such lateral grinding of the oversleeve onto the catheter over the barb may cause tearing of the catheter body.

Thus, an improved tunneler capable of securing a catheter at the proximal end of the tunneler without tearing the body or damaging the tip of the catheter may be desired. In particular, it may be desirable to minimize the abrasion caused by the lateral movement of the oversleeve, which can damage the outer circumferential surface of the catheter and compromises the integrity of the catheter body.

BRIEF SUMMARY OF THE INVENTION

Accordingly, described herein is a tunneler including an expandable attachment mechanism for securing a catheter onto the proximal end of a tunneler. In one aspect of the invention, the tunneler comprises an extension protruding from the proximal end thereof for insertion into the lumen of a catheter. The extension includes an expansion mechanism that allows it to expand laterally and/or radially inside the lumen of the catheter. The expansion mechanism may be further configured to interlock with an oversleeve, such that when the oversleeve is slid over the portion of the catheter positioned around the proximal end protrusion, the expansion mechanism expands and traps the catheter between the expansion mechanism and the inner wall of the oversleeve. Because a lateral force perpendicular to the axis of the tunneler is applied by the expansion mechanism from inside the lumen, grinding of the catheter's exterior surface by the oversleeve is minimized.

The tunneler may be further configured such that withdrawal of the oversleeve displaces the expansion mechanism and release the pressure on the inner wall of the catheter. Once the expansion mechanism has contracted, the catheter may then be easily removed. Furthermore, ribs, grooves or other surface profiles may be provided on the outer surface of expansion mechanism and/or the inner surface of the oversleeve to enhance the tunneler's ability to retain the catheter on the expansion mechanism.

In one variation, the tunneler comprises a protrusion extending from the proximal end of the tunneler body for insertion into the lumen of a catheter. The protrusion further comprises a sliding cam forming an expansion mechanism on the protrusion. As the oversleeve of the tunneler engages the sliding cam, the overall cross-section of the protrusion expands, trapping the catheter wall between the sliding cam and the inner wall of the oversleeve and securing the catheter to the proximal end of the tunneler. As the oversleeve is withdrawn, it forces the displacement of the sliding cam toward the distal end of the catheter, thereby decreasing the overall cross-section of the protrusion and releasing the compression pressure on the catheter. The catheter may then be easily removed form the protrusion.

In another variation, the tunneler comprises a protrusion with an expandable sleeve. The core of the protrusion has a barb-shaped profile expanding radially along the length of the tunneler in the proximal direction. The expandable sleeve surrounds the core of the protrusion and expands radially when displace in the proximal direction. The protrusion along with its expandable sleeve is inserted inside the lumen of a catheter. As the oversleeve is slid forward in the proximal direction over a portion of the catheter, it engages the expandable sleeve and expands the expandable sleeve radially. As a result, the catheter wall is trapped between the outer surface of the oversleeve and the inner surface of the catheter lumen. When the oversleeve is removed, it forces the expandable sleeve to contract, thus allowing the release of the catheter.

In yet another variation, an expandable elastomeric ring is positioned at the proximal portion of the tunneler for attaching a catheter onto the tunneler. With the proximal portion of the tunneler inserted inside the catheter, the elastomeric ring is expanded to engage the inner wall of the catheter and secure the catheter on the proximal end of the tunneler. To release the catheter, the elastomeric ring is allowed to contract and thus relieving the pressure on the catheter's inner lumen surface.

The expandable attachment mechanism design implemented at the proximal end of the tunneler may provide various advantages, including, but not limited to: 1) minimizing the abrasion to the tip and the outer surface of the catheter due to placement and removal of the oversleeve; 2) providing an improved connection to the catheter because the compression force is applied directly in the radial direction from the inner catheter lumen; 3) providing some accommodation to variation in lumen sizes as the tunneler/catheter interface is expandable; 4) facilitating the placement and removal of the catheter onto and from the tunneler due to the expansion mechanism being in a contracted state during each procedure.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 1A illustrates one variation of a tunneler with an expandable attachment mechanism.

FIG. 1B illustrates the protrusion at the proximal end of the tunneler shown in FIG. 1A. The protrusion comprises a sliding cam slidably disposed on an arm extending from the proximal end of the tunneler.

FIG. 1C is a perspective view of the sliding cam of FIG. 1B.

FIG. 2A is a side view of another variation of a tunneler with a sliding cam. The sliding cam is shown in the contracted position resting at the base of the barb.

FIG. 2B is a semi-transparent view of the tunneler of FIG. 2A. The engagement of the sliding cam with barb is illustrated. The corresponding catheter is also shown.

FIG. 2C is the cross-sectional view of the tunneler taken at position A-A as illustrated in FIG. 2D. The view is shown down the longitudinal axis of the tunneler towards its proximal end.

FIG. 2D is the side view of the tunneler illustrating the location of the cross-section view of FIG. 2C. The protrusion of the tunneler is shown without its corresponding sliding cam.

FIG. 2E is a plain view of the sliding cam of FIG. 2A, shown from the proximal end of the device down the longitudinal axis.

FIG. 2F is a side view of the sliding cam of FIG. 2E.

FIG. 3A illustrates another variation of a tunneler with sliding cam. A cross-sectional view of the device is provided to illustrate the pin from the sliding cam being inserted within the barb.

FIG. 3B is a side view of the tunneler of FIG. 3A.

FIG. 3C is a frontal view of the sliding cam of FIG. 3A. The sliding cam is shown from the proximal end down the longitudinal axis of the device.

FIG. 3D is the side view of the sliding cam of FIG. 3C.

FIG. 3E illustrates the tunneler of FIG. 3A inserted inside the lumen of the catheter.

FIG. 3F is an expanded view the barb/sliding cam interface of FIG. 3E.

FIG. 3G illustrates the oversleeve engaging the sliding cam.

FIG. 3H illustrates the tunneler of FIG. 3G after the placement of the oversleeve to secure the catheter at the proximal end of the tunneler.

FIG. 5A illustrates another variation of an expansion mechanism comprising an expandable sleeve. The tunneler is shown with a catheter attached to the proximal end of the device.

FIG. 5B is a perspective view of the expandable sleeve from FIG. 5A.

FIG. 6A illustrates yet another variation of a tunneler with an expansion mechanism comprising an expandable sleeve.

FIG. 6B is a cross-sectional view of the tunneler shown in FIG. 6A.

FIG. 6C is a side view of the expandable sleeve from FIG. 6A. The expansion slit of the sleeve is located along the length of the sleeve "A-A."

FIG. 6D is a cross-sectional view of the expandable sleeve of FIG. 6C.

FIG. 6E illustrates the engagement of the oversleeve with the expandable sleeve prior to the displacement of the expandable sleeve in the axial direction.

FIG. 6F illustrates the tunneler of FIG. 6E with the oversleeve and the expandable sleeve in the locking position securing the catheter.

FIG. 7A illustrates another variation of an expandable sleeve positioned on a barb at the proximal end of the tunneler.

FIG. 7B is a cross-sectional view of the tunneler of FIG. 7A.

FIG. 7C is an end view of the expandable sleeve from FIG. 7A.

FIG. 10 illustrates another variation of a tunneler with an expandable attachment mechanism. In this variation, the oversleeve is configured to accommodate a dual lumen catheter with a staggered tip.

FIG. 11A illustrates another variation of a tunneler, where an O-ring based expandable attachment mechanism is implemented at the proximal end of the tunneler.

FIG. 11B shows an expanded view of the proximal portion of the tunneler illustrated in FIG. 11A.

DETAILED DESCRIPTION OF THE INVENTION

Figure 4A:
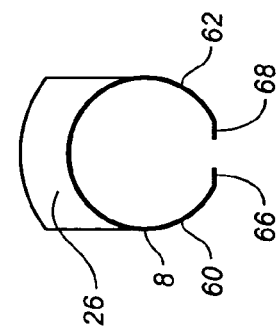
FIG. 4A illustrates another variation of a sliding cam designed to wrap around the barb. A side view of the sliding cam is shown.

The following detailed description should be read with reference to the drawings, in which like elements in different drawings may be identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, tubing or other elongated material/devices for insertion of such material/devices into a patient's body. Furthermore, it is to be understood that the tunneler described herein is not limited to applications where the tunneler is attached to the distal end of the catheter. One of ordinary skill in the art having the benefit of the disclosure herein would appreciate that the tunneler may be attached to a catheter via either the catheter's distal or proximal lumen.

It must also be noted that, as used in this specification and the appended claims, the singular forms "a," "an" and "the" include plural referents unless the context clearly dictates otherwise. Thus, for example, the term "an arm" is intended to mean a single arm or a combination of arms, "a fluid" is intended to mean one or more fluids, or a mixture thereof. Also, the terms, "tunneler" and "tunneling device" are used interchangeably herein. Furthermore, the words "proximal" and "distal" refer to directions closer to and away from, respectively, a physician that would operate the catheter when it's implanted, with the tip-end (i.e., distal end) of the catheter inserted inside a patient's body. Thus, for example, the catheter end placed close to the proximity of the heart of the patient would be the distal end of the catheter, while the catheter end outside the patient's body would be the proximal end of the catheter. For a tunneler, the tip end that is inserted first into a patient's body to create the tunneling channel in the tissue would be the distal end, and the opposite end of the tunneler where the catheter is attached is the proximal end.

In one aspect of the invention, an expandable attachment mechanism comprises a sliding cam positioned at the proximal end of a tunneler. In one particular variation, the tunneler comprises an elongated body with a tapered distal end for insertion into a bodily tissue. The elongated body may be fabricated from surgical steel or other metallic and/or polymeric materials with proper strength to support forces needed to separate tissues such that the tunneler may pass through. The distal portion of the tunneler body may be configured with a slight bend to facilitate insertion.

Referring now to FIG. 1A, an expansion mechanism 4 protrudes from a base 6 at a proximal end 12 of a tunneler body 2. The expansion mechanism 4 comprises a sliding cam 8 positioned on a post 10. The post 10 expands laterally (+Y) along the proximal direction (−Z), forming an incline 14 along the length of the proximal portion of the tunneler. The sliding cam 8 is slidably disposed on the incline 14. As the sliding cam 8 is slid towards the proximal direction (−Z), the overall cross-section of the protruding unit (i.e., the protrusion plus the sliding cam) increases. As the sliding cam 8 is slid back towards the base of the post (i.e., towards the distal direction, +Z) the overall cross-section of the protruding unit decreases.

As shown in FIG. 1B, the sliding cam 8 comprises an arm 16 that engages the post 10 of the tunneler. The arm 16 extends from the base 18 of a wedge-shaped body 20, as shown in FIG. 1C. Horizontal extensions 22, 24 are provided at the far end of the arm 16. When the sliding cam 8 is inserted on the post 10, the horizontal extensions 22, 24 secure the sliding cam 8 on the post 10 and prevent the sliding cam 8 from slipping. A tab 26, which extends laterally, is provided on the sliding cam 8 for engaging the oversleeve 28. Referring back to FIG. 1A, when the sliding cam 8 is located at the base 30 of the post 10, the protruding unit is contracted with a small cross-sectional area and can be easily inserted inside the lumen of a catheter 32. An oversleeve 28 that is slidably disposed on the elongated body 2 of the tunneler may then be advanced in the proximal direction of the tunneler. As the oversleeve 28 is advanced over the expansion mechanism 4, the oversleeve 28 engages the tab 26 on the sliding cam 8 and forces the sliding cam 8 to move on the incline 14 in the proximal direction. As the sliding cam 8 moves on the incline 14, it displaces in the lateral direction, applying pressure on the inner surface 34 of the catheter wall 36. This expansion pressure allows the tunneler to secure the catheter 32 to its proximal end. Optionally, the oversleeve 28 may be configured with an inner diameter that is slightly larger than the outer diameter of the catheter 32, such that the expansion of the sliding cam 8 forces the outer surface 38 of the catheter 32 onto the inner surface 40 of the oversleeve 28. As the sliding cam 8 continues to expand laterally, the wall of the catheter 32 is trapped between the outer surface of the sliding cam 8 and the inner surface of the oversleeve 28.

To remove the catheter 32, the oversleeve 28 is withdrawn and the sliding cam 8 is released. In one variation, the operator can pull off the oversleeve 28 to expose the sliding cam 8. The operator may then push the tab 26 on the sliding cam 8 in the distal direction (+Z) and force the sliding cam 8 to slide down the incline 14 and release the pressure on the inner surface of the catheter lumen. In another variation, an optional notch 42, groove, or other surface profile may be provided on the inner surface 40 of the oversleeve 28 for engaging the tab 26 on the sliding cam 8. When the oversleeve 28 is pulled off, the notch 42 applies a pressure on the tab 26 of the sliding cam 8 and forces the sliding cam 8 to displace in the distal direction. Once the sliding cam 8 is displaced, the pressure on the catheter wall 36 is released and the catheter 32 may then be easily removed.

In another variation, the post extending from the proximal end of the tunneler comprises a barb-shaped body 44, as shown in FIG. 2A. A sliding cam 8 is slidably disposed on the barb-shaped body 44. FIG. 2B is a cross-sectional view showing the functionality of the sliding cam 8 in relation to the barb-shaped body 44. In this variation, the diameter of the barb "D" is slightly larger than the diameter of the catheter "d". The barb's outer diameter may be selected as to provide a slight friction fit when the barb is inserted inside the lumen of the catheter. In one particular design, D is equal or less than about 110% of d. When the barb 44 is larger than the lumen of the catheter 32, some force/pressure may be required to place the catheter over the barb. In another variation, the barb may be configured such that D is smaller or equal to d. FIGS. 2C and 2D illustrate the inner configuration of the barb 44. A slot 46 is provided at the center region of the barb to receive the arm extending from the sliding cam 8. The sliding cam is slidably disposed on the incline surface 45 on the upper portion of the barb 44. FIG. 2E illustrates the frontal view of the sliding cam 8, and FIG. 2F shows the side view. The arm 16 and the horizontal extensions 22, 24 may comprise a flexible material, such as plastic. In addition, the horizontal extension may be configured with and angled profile relative to arm 16 extending from the based of the sliding cam. The angle of the horizontal extensions 22, 24 may facilitate the insertion of the arm 16 on the sliding cam into the slot 46 on the barb 44. The upwardly angled horizontal extensions 22, 24 may engage the base of the barb 44 and maintain a tension on the cam to keep the cam on the incline surface 45. When the sliding cam is slid toward the proximal end of the tunneler, the two horizontal extensions flap downwards as the wedge shaped portion of the cam is displaced on the incline surface 45 and pulls the arm 16 upward into the slot 46. The wedge-shaped portion 20 of the sliding cam may comprise a plastic material as well. In another variation, the wedge shaped portion 20 may comprise a metallic material while a polymeric arm 16 is joined to the base of the cam.

Referring now to FIG. 3A, another variation of the sliding cam 8 is illustrated. In this variation, the sliding cam 8 has a pin 48 extending proximally from the base of the sliding cam 8. An orifice 50 is provided on the center region of the barb 44 for receiving the pin 48 on the sliding cam 8, thus preventing the sliding cam 8 from detaching from the barb 44. As shown in FIG. 3B, an incline 14 is provided on the barb 44 so that the sliding cam 8 is displaced laterally as it is pushed toward the proximal end 52 of the device by the oversleeve 8. FIG. 3C shows the sliding cam 8 from its proximal end down the length of the sliding cam. FIG. 3D shows the same sliding cam 8 from the side. As illustrated, the pin 48 is centrally positioned and extends in the axial direction for engaging the barb 44.

FIG. 3E shows the sliding cam 8 in a contracted position at the base of the barb 44, the barb 44 along with the sliding cam 8 having been inserted inside the lumen 54 of a catheter 32. In this particular design, the barb/sliding cam 44, 8 unit has a slightly larger diameter than the catheter lumen 54, thus requiring the operator to apply some pressure to insert the barb/sliding cam 44, 8 into the lumen 54 of the catheter 32. In another variation, barb/sliding cam 44, 8 unit in the retracted state may be configured to be the same size as the inner diameter of the catheter 32. An oversleeve 28 is slidably disposed on the elongated body 2 of the tunneler. FIG. 3F is an expanded view showing the barb/sliding cam interface. The pin 48 extending from the base of the sliding cam 8 has a smaller diameter than the orifice 50 in the barb 44 for receiving the pin. As shown in FIG. 3F, a gap 56 is available between the top of the pin 48 and the upper surface 58 of the orifice 50 such that the sliding cam 8 may be displaced laterally in the upward direction. As the sliding cam 8 is displaced along the incline 14 on the barb 44, the pin 48 travels further into the orifice 50 on the barb 44 while being displaced upward. Once the pin 48 contacts the upper surface 58 of the orifice 50, the sliding cam 8 is prevented from further movement in the distal direction. This design may prevent the sliding cam 8 from over-expansion and damaging of the catheter 32.

FIG. 3G illustrates the oversleeve 28 engaging the sliding cam 8 prior to the displacement of the sliding cam 8. FIG. 3H illustrates the full displacement of the sliding cam 8. As shown, the catheter wall 36 is compressed between the outer surface of the sliding cam 8 and the inner surface of the oversleeve 28. Once the sliding cam 8 is prevented form further displacement, the oversleeve 28, which engages the sliding cam 8, is prevented from further advancement. This may indicate to the operator that the catheter 32 has been secured onto the tunneler. In addition, ribs, grooves or other surface profile may be provided on the inner surface 40 of the oversleeve 28 and/or the outer surface of the sliding cam 8 to increase friction between the oversleeve/catheter 32 and/or catheter 32/sliding cam. The ribs may improve the tunneler's ability to retain the catheter 32. Referring back to FIG. 3G, a notch 42 or other locking interfaces may be provided on the inner surface of oversleeve 28 for engaging the sliding cam 8. The tab 26 on the sliding cam 8 which extends radially allows the sliding cam to interface with the oversleeve 28. The notch 42 locks onto the tab 26 on the sliding cam 8 and the oversleeve 28 pushes the sliding cam 8 forward to secure the catheter 32. After the catheter 32 has been tunneled through the tissue, the catheter 32 is released by pulling the oversleeve 28 in the distal direction. The notch 42 on the oversleeve 28, which is still interlocked with the tab 26 on the sliding cam 8, forces the sliding cam 8 to displace in the distal direction, forcing the sliding cam 8 to slide down the incline 14 on the barb 44 and release the pressure on the inner wall of the catheter 32. The operator may then remove the catheter 32 from the barb 44.

Figure 4B:
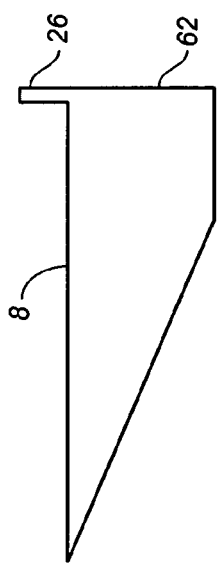
FIG. 4B is an end view of the sliding cam of FIG. 4A.
Figure 4C:
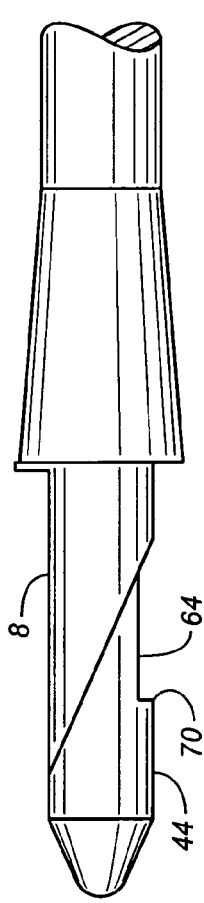
FIG. 4C illustrates the sliding cam of FIG. 4A positioned on a barb-shaped protrusion of the corresponding tunneler body.
Figure 4D:
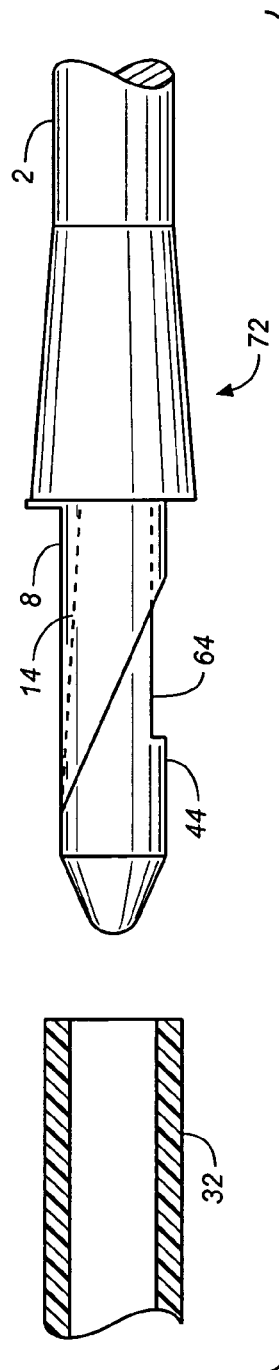
FIG. 4D is a cross-sectional view of the tunneler of FIG. 4C, shown with its corresponding catheter.

FIG. 4A illustrates another variation of a sliding cam 8. The sliding cam 8 is designed to surround a portion of the barb 44 to secure the sliding cam on the barb. As shown in FIG. 4B, two arms 60, 62 loop downward and are capable of reaching the lower portion of the barb. The arms 60, 62 may comprise a relatively flexible material such that they may be temporarily pulled apart for the placement of the sliding cam on the barb. A tab 26 is provided on the sliding cam for engaging the oversleeve. An indentation 64 on the underside of the barb 44 is provided to receive the distal ends 66, 68 of the sliding cam arms 60, 62. The indentation 64 may be configured with a surface profile matching the inner surface of the distal ends 66, 68 of the arms 60, 62 to improve the arm/barb interface. In addition, as shown in FIG. 4C, a ledge 70 may be provided at the proximal end of the indentation 64 to prevent the sliding cam 8 from over-sliding in the proximal direction. FIG. 4D shows the cross-sectional view of the tunneler 72 with a corresponding catheter 32. The sliding cam 8 sits on an incline surface 14 on the barb 44, such that when the sliding cam 8 is advanced in the proximal direction of the tunneler 72, the sliding cam 8 is also displaced in the lateral direction perpendicular to the axis of the elongated tunneler body 2.

In another aspect of the invention, the tunneler comprises a protrusion 80 with an expandable sleeve 82 positioned at the proximal end 84 of an elongated tunneler body 88. In one variation, the protrusion 80 comprises a barb 86 extending from the proximal end 84 of the elongated tunneler body 88 and a sleeve or sheath 82 slidably disposed around the base of the barb, as shown in FIG. 5A. The barb 86 may include a built-in compression slit or gap 92 to accommodate the advancement of the expandable sleeve 82 onto the head 94 of the barb 86. The expandable sleeve 82 may include one or more expansion slits 96, 98, 100, 102, 104 as illustrated in FIG. 5B. While the expandable sleeve 82 is positioned on the neck 90 of the barb 86, the sleeve is in a contracted position, which allows the barb 86 and its corresponding sleeve 82 to be easily inserted inside the lumen of a catheter 102. The head 94 of the barb 86 may include a slightly larger diameter then the lumen diameter of the catheter 106, such that the operator needs to apply some pressure to insert the tunneler into the catheter lumen. In another variation, the tunneler may be configured with a barb that has a head diameter that is equal to or smaller than the diameter of the catheter lumen. Once the catheter 106 is placed over the proximal end of the tunneler, the user may advance the oversleeve 110 in a proximal direction. In the advancement process, the oversleeve 110 engages the expandable sleeve 82 by pushing on a tab 112 extending therefrom, and displaces the expandable sleeve 82 in the proximal direction. As the expandable sleeve 82 moves from the neck 90 of the barb 86 toward the head 94 thereof, the expanding profile of the barb 86 forces the expandable sleeve 82 to expand radially, and pushes on the inner wall of the catheter 106. The wall of the catheter 106 is trapped between the outer surface of the expandable sleeve 82 and the inner surface of the oversleeve 110, thus securing the catheter 106 at the proximal end of the tunneler. In addition, ribs, grooves or other surface profiles may be provided on the inner surface of the oversleeve 110 and/or the outer surface of the expandable sleeve 82 to improve the retention of the catheter 106.

Furthermore, a notch 108 or other locking interface may be provided on the inner surface of the oversleeve 100 to engage the tab 112 on the expandable sleeve 82 when the oversleeve 110 is retracted. As the operator pulls on the oversleeve 110, the notch 108 engages the expandable sleeve 82 and displaces the expandable oversleeve 110 toward the distal end of the tunneler. Because the base 114 of the barb neck 90 prevents the expandable sleeve from further displacement, the oversleeve 110 may be completely removed from the proximal portion of the tunneler as the notch 90 on the oversleeve 110 disengages the tab 112 on the expandable sleeve 82.

In another variation, the expandable sleeve 82 has a single expansion slit 116 running along the length of the sleeve 82. Referring to FIG. 6A, the single slit expansion sleeve 82 is shown positioned over its corresponding barb 86 on the proximal end 118 of a tunneler. FIG. 6B is a cross-sectional view showing the sliding interface between the expandable sleeve 82 and the barb 86. FIG. 6C is a side view of the expandable sleeve 82, showing the expansion slit 116 running from the proximal end 120 of the expansion sleeve 82 to the distal end 122 of the expansion sleeve 82. At the distal end 122 of the sleeve a continuous tab 124 expands radially outward for engaging the oversleeve 110. FIG. 6D is a cross-sectional view of the expandable sleeve 82, illustrating a narrowing profile 128 in the inner lumen 126 of the sleeve 82, which matches the inclining outer surface of the barb 86. The narrowing profile 128 within the lumen of the sleeve allows the outer surface 130 of the sleeve 82 to expand evenly when it is advanced along the length of the barb 86. FIG. 6E shows the tunneler with the single slit expansion sleeve 82 attached to a catheter 106; the oversleeve 110 is shown engaging the tab 124 on the expandable sleeve 82 prior to the displacement of the expandable sleeve 82. FIG. 6F shows the expandable sleeve 82 fully displaced and trapping the wall 132 of the catheter 106 between the expandable sleeve 82 and the oversleeve 110.

FIG. 7A illustrates another variation of the expandable sleeve 82. The expandable sleeve 82 is shown disposed on the neck of a barb 86, extending from the proximal end 134 of the tunneler 136. FIG. 7B is the cross-sectional view of FIG. 7A. In this particular variation, the neck region 138 of the barb 86 has a constant diameter matching the lumen of the expandable sleeve 82, which also has a constant diameter along its length. A single tab 112 is provided at the distal end of the expandable sleeve 82 for engaging the oversleeve 110, as shown in FIG. 7C. When the expandable sleeve 82 is positioned on the neck of the barb 86, the tab 112 extends beyond the periphery of the tunneler, such that the tip portion of the tab 112 engages the oversleeve 110.

Figure 8C:
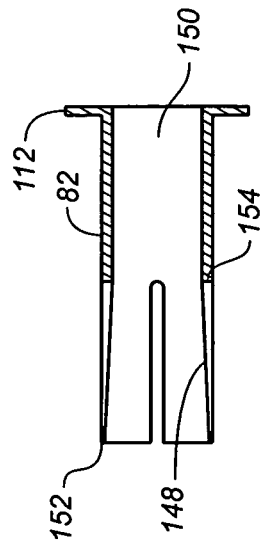
FIG. 8C is the cross-sectional view of the expandable sleeve of FIG. 8B.
Figure 8B:
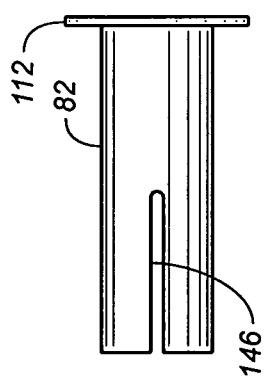
FIG. 8B is the side view of the expandable sleeve of FIG. 8A.
Figure 8A:
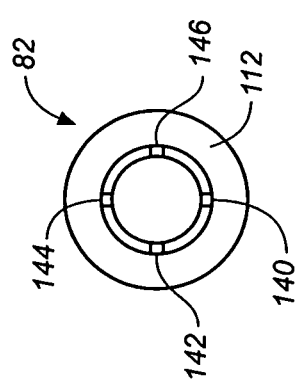
FIG. 8A is a frontal view of another variation of an expandable sleeve. The device is shown from the proximal end down the longitudinal axis of the device.
Figure 8D:
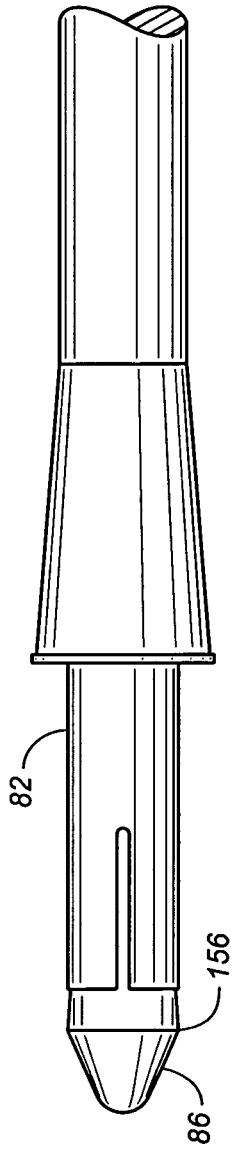
FIG. 8D illustrates the expandable sleeve of FIG. 8B disposed on a barb at the proximal end of a tunneler.

FIGS. 8A-8D illustrate another variation of an expandable sleeve 82. As shown in FIG. 8A, the expandable sleeve 82 has a plurality of expansion slits 140, 142, 144, 146. In this particular variation, the slits 140, 142, 144, 146 only extend halfway down the length of the sleeve 82, as shown in FIG. 8B. The inner wall 148 of the expandable sleeve 82 is configured, such that the diameter of the lumen 150 gradually decreases along the length of the sleeve 82 from the distal end 152 to the mid-section 154 of the sleeve 82, as illustrated in FIG. 8C. The slope on the inner catheter wall 148 may be configured to match the incline on the corresponding barb 86, such that the expandable sleeve 82 expands radially when it is advanced toward the head 156 of the barb 86. In FIG. 8D, the multi-slit expandable sleeve 82 is shown resting on the neck of a corresponding barb 86. A corresponding oversleeve, which may be used to engage the expandable sleeve 82, is not shown.

Figure 9A:
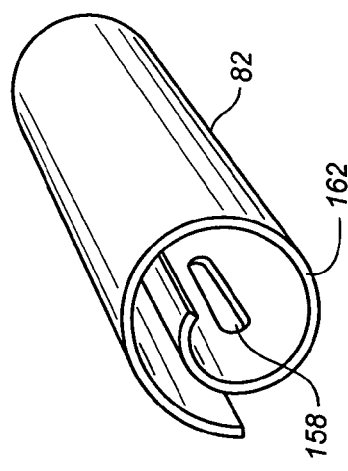
FIG. 9A shows yet another variation of an expandable sleeve.
Figure 9B:
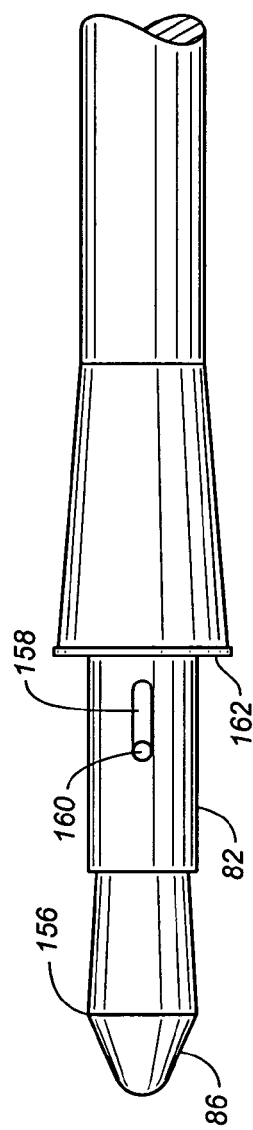
FIG. 9B illustrates the expandable sleeve of FIG. 9A positioned on a corresponding barb at the proximal end of a tunneler. As shown, a pin on the barb is positioned within the guiding slot of the expandable sleeve.
Figure 9C:
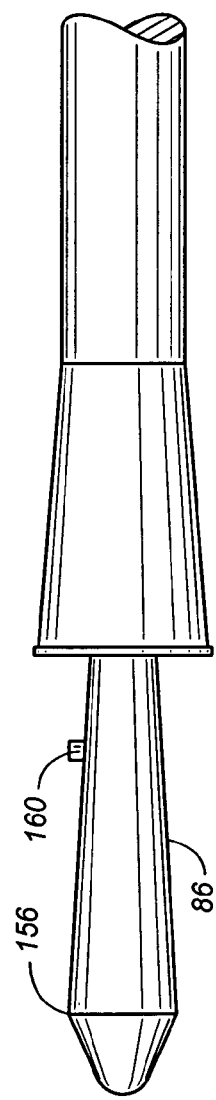
FIG. 9C shows the proximal end of the tunneler from FIG. 9B without its expandable sleeve.

In FIG. 9A, yet another variation of an expandable sleeve 82 is shown. In this variation, the expandable sleeve 82 comprises a continuous layer of material which curls around itself. In one particular design, the spiral sleeve 82 comprises a flexible sheet of plastic that maintains the spiral-shape in the relaxed state. A slot 158 may be provided to match a pin 160 positioned on the corresponding barb 86 to guide the sliding of the spiral sleeve 82 over the barb 86, as shown in FIG. 9B. Movement of the sleeve 82 towards the head 156 of the barb 86 causes radial expansion of the sleeve 82. The pin 160 on the barb 86 may prevent over advancement of the spiral sleeve 82. FIG. 9C shows the barb 86 without the spiral sleeve. Optionally, a tab or a pin may be provided at the distal end 162 of the spiral sleeve 82 so that the spiral sleeve 82 can engage an oversleeve, which may be slidably disposed on the shaft of the tunneler.

In another aspect of the invention, the tunneler 170 with an expandable attachment mechanism 172 is configured to receive a multi-lumen catheter 174 including staggered lumen openings 176, 178 at the distal portion of the catheter 174. In one variation, the oversleeve 180 has a staggered inner lumen 182 to accommodate a dual lumen catheter with a staggered tip 174 (e.g., a Hickman® dual lumen catheter, BARD Access Systems, Salt Lake City, Utah, etc.), as shown in FIG. 10. The expansion mechanism 172 at the proximal end of the tunneler 170 is inserted into the distal lumen 176 of the catheter 174. The oversleeve 180 is advanced toward the catheter 174, engages the expansion mechanism 172, and secures the distally extending tube 184 of the catheter between the expansion mechanism 172 and the inner wall on the narrowed section 186 of the oversleeve 180. The proximal/wide section 188 of the oversleeve 180 has a lumen with a larger diameter to accommodate the staggered profile of the catheter, which houses the proximal lumen 178 of the catheter 174. Thus, as the oversleeve 180 is advanced forward, the proximal portion of the catheter is able to go over the proximal lumen opening 178 and cover the staggered profile at the distal portion of the catheter.

In yet another variation, the tunneler 200 comprises an elongated body 202 with an expandable O-ring 204 positioned at the proximal portion 206 of the elongated body 202, as shown in FIG. 11A. The distal portion 208 of the elongated body 202 may be tapered to facilitate the insertion of the tunneler into a tissue in the patient's body. In another variation, the distal portion 208 of the elongated body 202 may be attached to a handle 210, as illustrated in FIG. 11A. The surgeon may utilize the tunneler 200 by gripping onto the handle 210. For example, once a subcutaneous tunnel has been established within a patient's body, the surgeon can hold onto the handle 210 and insert the proximal end 212 of the tunneler into a first incision site of the subcutaneous tunnel, advance the tunneler through the subcutaneous tunnel, and allow the proximal portion 206 of the tunneler 200 to exit the tunnel through a second incision site of the subcutaneous tunnel. A catheter may then be attached to the proximal end 212 of the tunneler 200. Once the catheter is attached to the tunneler 200, the surgeon holds onto the handle 210 and pulls the catheter through the subcutaneous tunnel and exiting at the first incision site. The catheter is then released from the tunneler. Although the elongated body of the tunneler is shown as a straight rod in FIG. 11A, one of ordinary skill in the art, having the benefit of this disclosure, would appreciate that in some applications it may be beneficial to provide a curvature on the elongated body 202. One of ordinary skill in the art would also appreciate that the handle-design may also be implemented with other expansion mechanism, and it is not limited to application with an O-ring based expansion mechanism.

As discussed earlier, the expansion mechanism, such as the expandable O-ring, may be configured for insertion into the proximal end of a catheter. In some variations, the lumen of the catheter is exposed at the proximal end of the catheter, such that the expansion mechanism may be directly inserted into the lumen of the catheter. In other variations, the proximal end of the catheter may include a hub (e.g., housing, connection adaptor, etc.) with an inner surface (e.g., undercut), which faces towards the longitudinal axis of the catheter, at the proximal end of the hub. The catheter may include one or more lumens. The expansion mechanism at the proximal end of the tunneler may be configured for insertion into the proximal end of the hub. Once the expansion mechanism is within the proximal end of the hub, the expansion mechanism may be expanded to engage the inner surface of the hub, and secure the hub at the proximal end of the catheter to the tunneler. The catheter may then be reverse tunneled through the tissue on the patient's body.

Referring now to FIG. 11B, the proximal portion 206 of the tunneler 200 with an O-ring 204 expansion mechanism is shown. The proximal tip 212 of the tunneler can be inserted into the lumen of a catheter. Once the proximal portion 206 of the tunneler 200 is inside the lumen of the catheter, the elastomeric ring 204 (e.g., a ring comprises a polymeric material, etc.) positioned on the proximal portion 206 of the tunneler 200 is expanded (i.e., radially away from the longitudinal axis 214 of the tunneler 200) inside the catheter and engages the inner catheter wall. The radial pressure from the elastomeric ring 204 secures the catheter on the proximal end of the tunneler. Although the elastomeric ring 204 shown in FIG. 11B has a circular cross-section, one of ordinary skill in the art having the benefit of this disclosure would appreciate that the elastomeric ring 204 may be configured with various cross-sectional shapes (e.g., oval, octagonal, etc.). Once the catheter is pulled through the subcutaneous tunnel, the axial force on the elastomeric ring 204 may be removed allowing the elastomeric material to recover its original shape, and thereby release the catheter from the proximal end 212 of the tunneler 200. One of ordinary skill in the art having the benefit of this disclosure would appreciate that various compression and/or expansion mechanisms that are well know to one of ordinary skill in the art may be implemented on the distal portion of the tunneler's elongated body to expand the elastomeric ring.

Figure 11C:
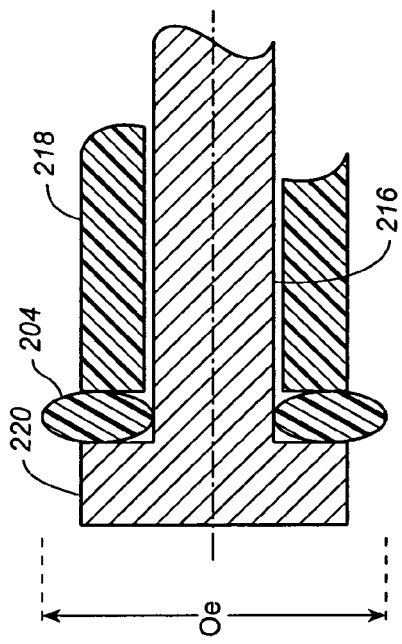
FIG. 11C is a cross-sectional view illustrating an O-ring of the expansion mechanism in a relaxed state.
Figure 11D:
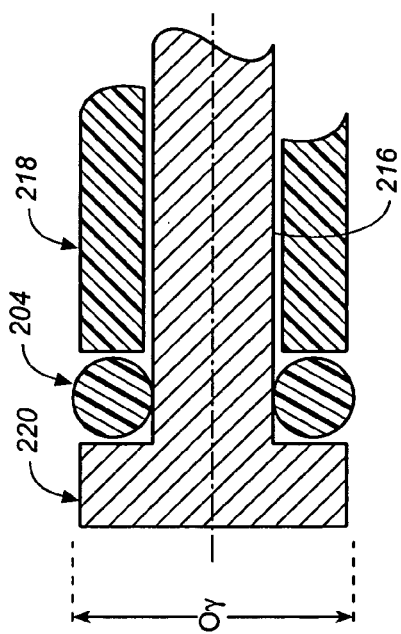
FIG. 11D is a cross-sectional view illustrating the O-ring of FIG. 11C in an expanded (i.e., actuated) state, with the outer diameter of the O-ring expanding radially away from the longitudinal axis of the tunneler.

In one variation, a compression mechanism is provided to apply an axial force to compress the elastomeric ring 204 and force the elastomeric ring 204 to expand radially. FIG. 11C shows the elastomeric ring 204 in an uncompressed relaxed state having an outer diameter Or. As axial force is applied onto the elastomeric ring 204, the compression forces the outer periphery of the ring 204 to expand and assume an outer diameter Oe in the expended state, such that Oe>Or. Once the axial force is removed, the elastomeric ring relaxes back to about the original size, Or. In the example illustrated in FIG. 11C, the elastomeric ring 204 is position on the shaft 216 of the tunneler, and a sleeve 218 movably disposed on the shaft 216 is provided for compressing the elastomeric ring 204 against the proximal portion 220 of the shaft 216. As the sleeve 218 is displaced proximally, as shown in FIG. 11D, the elastomeric ring 204 is compressed between the shaft 216 and the sleeve 218, and expands radially. Various locking mechanisms (e.g., threaded feature, cam feature, etc.) that are well known to one of ordinary skill in the art may be implemented to retain the sleeve 218 in the proximally displaced position, such that axial pressure can be maintained on the elastomeric ring 204. To release a catheter or other device attached to the proximal end of the tunneler, the sleeve 218 is displaced forward toward the distal end of the tunneler. Once the axial pressure is removed, the elastomeric ring 204 contracts and returns to its original relaxed-shape.

In another variation, threaded features are provided on the shaft 216 of the tunneler and the inner surface of the corresponding sleeve 218, which is positioned over the shaft 216, such that rotation of the sleeve 218 relative to the shaft 216 in one direction advances the sleeve proximally, and rotation in the opposite direction retracts the sleeve. In another variation, a cam is implemented on the shaft 216 of the tunneler, and interfaces with the sleeve 218, such that the sleeve 218 can be advanced proximally to apply an axial force on the elastomeric ring.

Figure 11E:
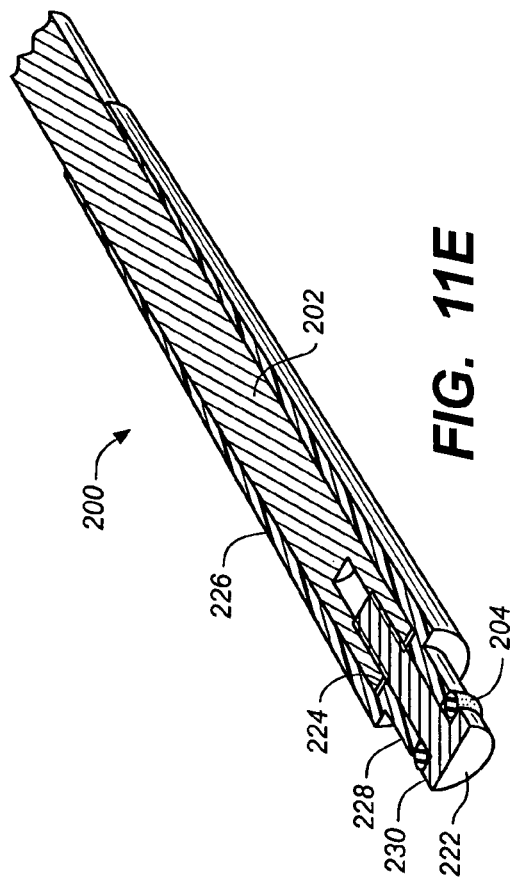
FIG. 11E is a cross-sectional view of the proximal portion of a tunneler with an expanding O-ring mechanism.

In yet another variation, a screw 222 is secured on the proximal end 224 of the elongated body 202 of a tunneler 200 as shown in FIG. 11E. Cam features are provided on the elongated body 202 of the tunneler as well as the sleeve, which comprises an overmold 226, such that displacement of the overmold 226 relative to the elongated body 202 engages the cam action and compress the O-ring 204 between the proximal end 228 of the over mold 226 and the head 230 of the screw. The operator may hold the elongated body 202 of the tunneler and rotate the overmold 226 to compress the screw 222 between the head 230 of the screw and the overmold 226. In another variation, the operator may rotate the elongated body 202 and hold the overmold 226 in place to apply an axial force on the O-ring 204.

In another design variation, a thread is provided along length of a screw. The distal end of the screw is slidably secured within the proximal end of the elongated body (e.g., shaft) of the tunneler. The screw is configured with a distal end that engages the elongated body an prevents the screw from rotating about the axis of the tunneler. An overmold is positioned around the elongated body of the tunneler, and the proximal portion of the tunneler interfaces with the screw. The inner surface of the overmold, which engages the screw, is provided with a matching thread pattern, such that rotation of the overmold in one direction retracts the screw toward the elongated body of the tunneler, while rotation of the over mold in the opposite direction advances the screw away from the elongated body of the tunneler. As the screw is retracted, it compresses the O-ring against the proximal end of the overmold. As the screw is advance proximally, the pressure on the O-ring is released.

The tunneler with an expandable attachment mechanism may be implemented for tunneling various catheters or other elongated material/devices through a patient's bodily tissue. In one approach, a first incision is made close to the patient's left nipple, and a second incision is made close to the left clavicle for accessing the subclavian vein. The proximal end of the tunneler is placed inside the lumen at the distal tip of a catheter. An oversleeve, which is slidably disposed on the shaft of the tunneler, is advanced toward the proximal end of the tunneler to engage the expansion mechanism located at the proximal end of the tunneler. The catheter is secured between the expansion mechanism and the oversleeve after the oversleeve has been slid into place. The distal end of the tunneler is then inserted into the first incision. The tunneler may be used to create a path between the first incision and the second incision. The tunneler is pushed through the tissue to exit at the second incision. The tunneler is pulled out of the second incision, pulling a distal portion of the catheter through the tunneled channel between the first and second incision. The oversleeve is pushed toward the distal end of the catheter to displace the expansion mechanism and release the pressure on the inner lumen surface of the catheter. The distal end of the catheter can then be removed from the tunneler. A guidewire, introducer, and tear-away sheath may then be implemented to insert the distal portion of the catheter into the patient's circulatory system through the exposed subclavian vein, after which the physician may advance the tip of the catheter towards the superior vena cava-right atrial junction. Once the catheter is positioned in a predetermined location, sutures may be used to close the incision sites as necessary.

In certain applications, it may be particularly desirable to tunnel a catheter by attaching the distal end of the catheter to the tunneler, instead of using the proximal end of the catheter. For example, a catheter having an integral bifurcation on the proximal end of the catheter may be difficult to tunnel through the tissue from its proximal end. First, it may be hard to attach a tunneler to the bifurcate. In addition, the extension tubings coming off the bifurcate may prevent the physician from inserting the bifurcate through a narrow tunneling channel under the tissue. In these situations, securing the distal end of the catheter to the tunneler may be desirable. In another situation, where the catheter has a detachable bifurcation at the proximal end of the catheter, the physician may still choose to attach the tunneler to the distal end of the catheter, and tunnel the catheter from the exit incision site to the cut-down site before inserting the distal end of the catheter into the body. In another variation, the bifurcation may be removed so that the proximal end of the catheter may be attached to a tunneler. In this case, the proximal portion of the catheter is tunneled from the cut-down site to the exit incision site.

This invention has been described and specific examples of the invention have been portrayed. While the invention has been described in terms of particular variations and illustrative figures, those of ordinary skill in the art, will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. A tissue tunneler for tunneling a catheter subcutaneously under a patient's skin from a first incision point to a second incision point, the catheter including at least one lumen, the tissue tunneler comprising:
    an elongated body comprising a tapered distal end to facilitate insertion of the tunneler into a body tissue and minimize trauma to the patient, the elongated body capable of creating a subcutaneous tunnel while minimizing trauma to the patient, and a proximal end including a barb having an expanding cross-sectional area in a proximal direction, the barb having a proximal end with a diameter greater than a diameter of the the at least one lumen;
    an oversleeve slidably disposed over the elongated body; and
    an expansion mechanism slidably disposed about the barb, the expansion mechanism including an expandable sleeve having a smooth outer surface and a tab extending radially outward from the sleeve to engage an inner surface of the oversleeve following insertion of the barb and the expandable sleeve into the catheter lumen.

2. The tunneler according to claim 1, wherein the barb proximal end diameter is equal to or less than about 110% of the catheter lumen diameter.

3. The tunneler according to claim 1, wherein the expansion mechanism comprises a sliding cam.

4. The tunneler according to claim 3, wherein the barb includes an incline surface, the sliding cam slidably disposed on the incline surface.

5. The tunneler according to claim 4, wherein the sliding cam comprises a wedge-shaped body and an extending arm at a base of the wedge-shaped body, the barb including a slot that receives the extending arm.

6. The tunneler according to claim 5, wherein the sliding cam further comprises extensions at an end of the extending arm opposite the wedge-shaped body.

7. The tunneler according to claim 3, wherein the sliding cam comprises a wedge-shaped body and a pin extending in an axial direction of the elongated body, the barb including a passage that receives the pin.

8. The tunneler according to claim 7, wherein the pin has an outer diameter smaller than a diameter of the passage.

9. The tunneler according to claim 1, wherein the elongated body includes a rounded tip disposed proximal of the proximal end of the barb.

10. The tunneler according to claim 1, wherein the expandable sleeve comprises at least one expansion slit.

11. The tunneler according to claim 1, wherein the elongated body includes a rounded tip at a proximal-most end thereof.

12. The tunneler according to claim 1, wherein the barb has a frusto-conical shape.

13. The tunneler according to claim 1, wherein the expandable sleeve has a tubular body with an inner lumen including a gradually decreasing diameter from a proximal end of the tubular body to a distal end thereof.

14. The tunneler according to claim 13, wherein the tubular body defines a constant outer diameter.

15. The tunneler according to claim 14, wherein the tab has a circular shape with a diameter greater than the outer diameter of the tubular body.

16. A tissue tunneler for tunneling a catheter subcutaneously under a patient's skin from a first incision point to a second incision point, the catheter including at least one lumen, the tissue tunneler comprising:
    an elongated body comprising a tapered distal end to facilitate insertion of the tunneler into a body tissue and minimize trauma to the patient, the elongated body capable of creating a subcutaneous tunnel while minimizing trauma to the patient, and a proximal end including a barb having an expanding cross-sectional area in a proximal direction and a rounded tip disposed proximal of a proximal end of the barb;
    an oversleeve slidably disposed over the elongated body; and
    an expansion mechanism slidably disposed about the barb, the expansion mechanism including an expandable sleeve having a smooth outer surface and a tab extending radially outward from the sleeve to engage an inner surface of the oversleeve following insertion of the barb and the expandable sleeve into the catheter lumen.

17. A tissue tunneler for tunneling a catheter subcutaneously under a patient's skin from a first incision point to a second incision point, the catheter including at least one lumen, the tissue tunneler comprising:
    an elongated body comprising a tapered distal end to facilitate insertion of the tunneler into a body tissue and minimize trauma to the patient, the elongated body capable of creating a subcutaneous tunnel while minimizing trauma to the patient, and a proximal end including a barb having an expanding cross-sectional area in a proximal direction, the elongated body including a rounded tip at a proximal-most end thereof;
    an oversleeve slidably disposed over the elongated body; and
    an expansion mechanism slidably disposed about the barb, the expansion mechanism including an expandable sleeve having a smooth outer surface and a tab extending radially outward from the sleeve to engage an inner surface of the oversleeve following insertion of the barb and the expandable sleeve into the catheter lumen.

18. A tissue tunneler for tunneling a catheter subcutaneously under a patient's skin from a first incision point to a second incision point, the catheter including at least one lumen, the tissue tunneler comprising:
    an elongated body comprising a tapered distal end to facilitate insertion of the tunneler into a body tissue and minimize trauma to the patient, the elongated body capable of creating a subcutaneous tunnel while minimizing trauma to the patient, and a proximal end including a barb having an expanding cross-sectional area in a proximal direction;
    an oversleeve slidably disposed over the elongated body; and
    an expansion mechanism slidably disposed about the barb, the expansion mechanism including an expandable sleeve having a smooth outer surface and a tab extending radially outward from the sleeve to engage an inner surface of the oversleeve following insertion of the barb and expandable sleeve into the catheter lumen, the expandable sleeve having a tubular body with an inner lumen including a gradually decreasing diameter from a proximal end of the tubular body to a distal end thereof.

19. The tunneler according to claim 18, wherein the tubular body defines a constant outer diameter.

20. The tunneler according to claim 19, wherein the tab has a circular shape with a diameter greater than the outer diameter of the tubular body.

* * * * *